US00PP10839P

United States Patent [19]

Holder

[11] Patent Number: Plant 10,839

[45] Date of Patent: Mar. 23, 1999

[54] SUGAR CANE VARIETY CL77-797

[75] Inventor: David G. Holder, Clewiston, Fla.

[73] Assignee: U.S. Sugar Corporation, Clewson, Fla.

[21] Appl. No.: 598,558

[22] Filed: Feb. 8, 1996

[51] Int. Cl.[6] ..... A01H 5/00

[52] U.S. Cl. ..... Plt./100

[58] Field of Search ..... Plt./100

*Primary Examiner*—James R. Feyrer
*Attorney, Agent, or Firm*—Peter K. Trzyna

[57] ABSTRACT

A cross between a female variety known as CL61-620 with a mixture of male varieties has produced an improved variety of sugar cane.

7 Drawing Sheets

This invention relates generally to a new variety of sugar cane.

BACKGROUND AND SUMMARY OF THE INVENTION

This new variety of sugar cane with the identifying number CL77-797 originated as a seedling produced by the inventor by crossing the variety CL61-620 as a female with a mixture of varieties as male. In this form of variety designation, which is well known to sugar cane breeders, "CL" denotes the breeding locality or station, i.e. Clewiston, Fla.; 77 represents the year that the particular variety was first grown, i.e. 1977; and 797 is the distinctive number assigned to that variety among those grown in that year. The cross was made in December 1975, at Clewiston, Fla. and this new variety was selected from among the progeny of the cross. The inventor has subsequently asexually reproduced the new variety at Clewiston, Fla., by means of stem cuttings.

The new variety matures early (i.e. has commercially acceptable sucrose levels beginning in November), maintains a high level of sucrose throughout the harvest season (a typical harvest season is November 1 to March 15), produces high tons per acre of cane and high tons per acre of sugar. In a trial with six replications in a randomized complete-block design over three crops (i.e., three crops were harvested from the same six plots) on a medium mineral Terra Ceia organic soil, the new clone averaged higher in both early and late percent yield of sucrose (yield of 96° sucrose, percent cane) and higher in both early and late tons per acre of sucrose than standard cultivars CL61-620 and CP70-1133 . The new clone produced more tons per acre of cane than CP70-1133 and slightly less than CL61-620. In a trial with four replications in a randomized complete-block design extending over three crop years on a low mineral Terra Ceia organic soil, the new clone averaged higher in both early and late percent yield of sucrose than standard cultivars CL61-620 and CP72-1210. The new clone exceeded CP72-1210 in tons per acre of cane and both early and late tons per acre of sucrose. The new clone approached CL61-620 in tons per acre of cane, and both early and late tons per acre of sucrose. The new clone has been competitive with standard cultivars under large scale outfield testing practices. During the 1994-95 season CL77-797 was compared with both CL61-620 and CP80-1827 in the first crop of successively planted cane (successive planting refers to the cycle of planting in which the old stubble is disced out immediately after harvest, the field prepared for planting, then planted with sugar cane after only a few weeks). The large scale outfield testing fields, which varied from 35 to 70 acres each, were distributed over variable organic soil types, and varied in planting dates and harvest dates. CL77-797 averaged higher in percent yield of sucrose, tons per acre of cane, and tons per acre of sucrose than either CL61-620 or CP80-1827.

In one regular commercial planting following fallow in a 37-acre field, this new variety produced 88 tons per acre of cane and 9.8 tons per acre of sugar in a 17-month crop.

The new variety is not recommended for commercial use on sandy soils.

Based on experimental tests and extensive field observations the new variety is judged to be resistant to several diseases common to Florida. In inoculation tests the variety was highly resistant to smut (caused by *Ustilago scitaminea* Syd. and P. Syd.), resistant to ratoon stunting disease (caused by *Clavibacter xyli* subsp. *xyli*, Davis), resistant to leaf scald (caused by *Xanthomonas albilineans* Ashby, Dowson) and to sugarcane mosaic virus strains A, B, D, and E. In order to verify the inoculation tests, extensive field observations were made and the variety was found to maintain its resistance to the four diseases above under commercial cultural practices. Further, based on extensive field observations the new variety is judged to be resistant to rust disease (caused by *Puccinia melanocephala* Syd. and P. Syd.), eye spot disease (caused by *Bipolaris sacchari* (Butl.) Shoemaker), and brown stripe (caused by *Cochliobolus stenospilus* (Drechs.) Mat. and Yam. The new clone is subject to natural infections of pokkah being (caused by *Fusarium moniliforme* Sheldon).

It is therefore an object of the present invention to provide an improved variety of sugar cane.

Other objects and advantages of the invention will become apparent upon reading the following detailed description of the drawings and appended claim, and upon reference to the accompanying drawings.

BRIEF DESCRIPTION OF THE DRAWINGS

The invention is illustrated diagrammatically and photographically in the accompanying drawings wherein:

FIG. 1 is a photographic view of approximate midsections of typical stalks, showing internode 1, stem bud 5, growth ring 2, leaf scar 6, wax ring 4, and root band 3; two of the stalks (laid with buds at sides) illustrate the zig zag alignment of internodes.

FIG. 5 is a photographic view showing intermediate age cane illustrating that the cane has begun to lodge.

FIG. 6 is a photographic view of young cane showing that stalks on the outside of the stools bow outwardly near the base.

FIG. 7 is a photographic view including a representative 36.6-decimeter stalk of 16-month-old CL77-797 from a 65 ton-per-acre field illustrating the recumbent growth habit of mature stalks.

FIG. 8 is a photographic view of CL77-797 showing the recumbent growth habit of the new sugar cane after it was burned in preparation for harvest.

FIG. 9 is a photographic view illustrating the erectness of the leaf blade and the drooping tip.

DETAILED DESCRIPTION

Figure 2A:
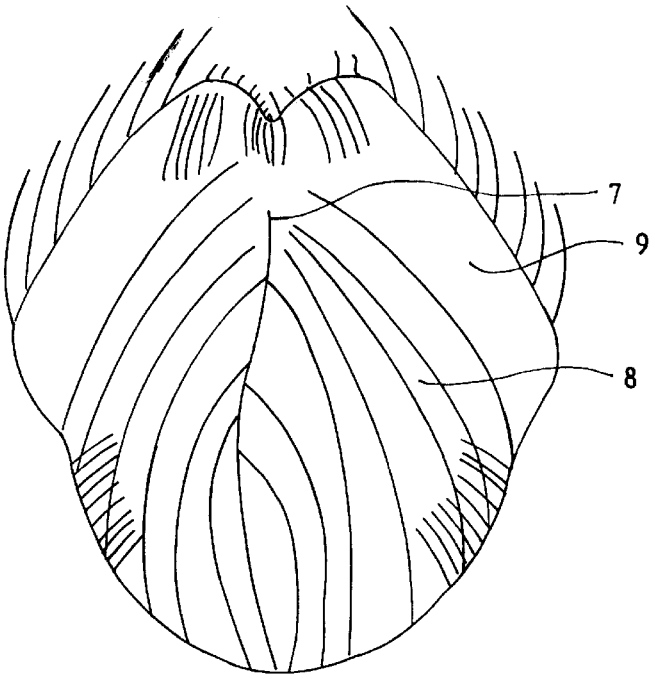
FIGS. 2A and 2B show the anterior (FIG. 2A) and posterior (FIG. 2B) views of the stem bud, showing germ pore 7, prophyll 8, and wing 9.
Figure 4:
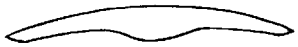
FIG. 4 is a view showing the outline of a ligule after its removal from the inner surface of the leaf sheath.
Figure 2B:
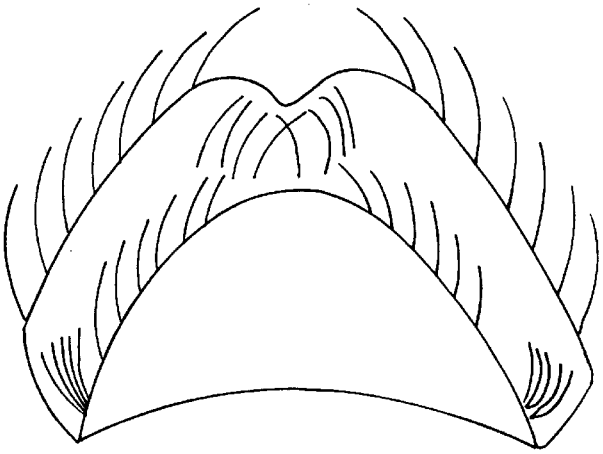
Figure 3:
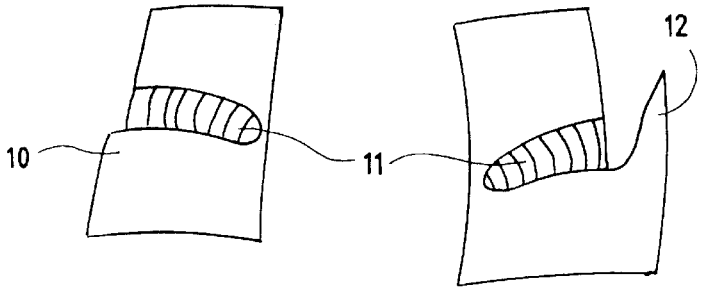
FIG. 3 is a view of the two separated and flattened halves of the upper part of a leaf sheath, showing the outer aurice 10, the inner auricle 12, and the dewlap or blade joint 11.

In the following detailed description of the new variety of sugar cane, the terminology employed in morphological description and numbering of hair groups is that employed by Artschwager. (See Sugarcane (*Saccharum officinarum* L.: Origin, Classification, Characteristics, and Description of Representative Clones by Ernst Artschwager and E. W. Brandes. Agriculture Handbook No. 122. United States Department of Agriculture, 1958.) Color descriptions are made by referring to the plates of Maerz and Paul. (See A Dictionary of Color, second edition, by A. Maerz and M. Rea Paul. McGraw-Hill Book Company, 1950.)

The Stalk (or Culm)

Habit of growth: In commercial plantings emergence of the new variety is slower and after emergence the rate of growth in early season is average when compared to the current population of commercial varieties (based on observations of farm managers at the United States Sugar Corporation).

Stalks of young cane on the outside of the stools bow outwardly near the base (see FIG. 6). The stalks begin to lodge as the crop matures (see FIG. 5) and most are recumbent by time of harvest (see FIGS. 7 and 8). The new variety approximates CL61-620 in recumbency. It is more recumbent than CP80-1827. The internodes of the stalk are slightly zig zag in alignment (see FIG. 1). A typical angle formed by two internodes meeting at a node approximates 4.5 degrees, but angles of 2 degrees to 8 degrees are not unusual.

The new recumbent variety is harvested satisfactorily by the chopper type mechanical harvester currently in use in Florida. This one-row harvester is equipped with break away crop divider points and scrolls (twin spiral crop dividers) which operate between the rows and direct cane to the throat of the harvester where the base cutters are located. There have been no reports of brittleness for CL77-797 in the commercial harvest operations.

Based on a survey of farm managers at the United States Sugar Corporation, the new variety has fewer suckers (late produced stalks with low sucrose content) in commercial fields at harvest than standard varieties CL61-620 and CP80-1827. The new variety has fewer than the average number of stools pulled out of the ground by the mechanical harvester indicating a stronger than average root system. The new variety ratoons well after harvest; i.e. a high population of new shoots emerge in the regrowth.

Size: The stalks in mature plant cane averaged 32 decimeters long on medium mineral Terra Ceia organic soil and 25 decimeters long on low mineral Terra Ceia organic soil. They are near circular in cross section, averaging 27 millimeters (nonbud side) ×28.0 millimeters (bud side to bud side) in the middle part of the stalk. The larger diameter varied from 23.4 to 32.7 millimeters. The stalk diameter is considered of medium thickness when compared to the population of commercial varieties in Florida. It is slightly smaller in diameter than CL61-620.

Flesh: The color of the flesh often approximates Maerz and Paul's designation 9-C-1. The flesh may have a small hole in the center of a cross section. The stalk averages 10.6 percent fiber content.

Internodes: They are slightly concave convex in shape (see Artschwager and Brandes, p. 49, FIG. 10) and range from 8 to 13 centimeters long in the middle of the stalks, averaging 11. 5 centimeters. Usually bud furrows are shallow; they may vary from absent, short, or extend the length of the internode. Neither corky cracks nor growth cracks are evident. A moderately tall wax ring is usually apparent. The internodes are covered by a moderately heavy wax bloom.

Color: In actively growing stalks, the stem color of internodes near the top of the plant that are protected by a tight leaf sheath initially approximate Maerz and Paul's 10-F-1. Quickly the color of most internodes in this area darkens to approximate 18-1-2. In older areas of the stalk, a few internodes that have been protected by a tight leaf sheath may remain as light colored as Maerz and Paul's 10-G-2. After the sheath loosens, the color of the rind of most internodes progresses through shades of green with Maerz and Paul's 20-L-5 and 23-L-1 as most frequent colors. Internode rinds exposed to direct sunlight quickly assume a reddish blush due to anthocyanin pigments, then with lengthy exposure the rind color darkens to approximate Maerz and Paul's 8-L-4. The wax covering on the rind may become black from mold growth and completely mask the underlying stem color.

The initial color of the growth ring approximates Maerz and Paul's 9-H-3 but older growth rings may darken to approximate the color of the associated internode. The initial color of the root band approximates Maerz and Paul's 9-D-2 then the color may darken with age to approximate that of the associated internode.

Growth ring: It ranges from 2.4 to 5.5 millimeters in height and averages 3.3 millimeters. It is tumescent on older internodes. It is about the same color as the internode.

Root Band: It is taller on the bud side than the opposite side. It is 4.2 to 8.8 millimeters tall, averaging 6.6 millimeters when measured in the middle of the flat side. It is straight in the bud region and obconoidal opposite the bud. The color is lighter than the basic color of the internode. Usually two rows of root primordia are present; they may be irregular and the upper row may be lacking.

Leaf scar: The leaf scar protrudes and is oblique. It flares slightly under the bud.

Epidermal cells: The pattern of the stem epidermal cells is Artschwager's type 1 in which the small cell groups consist of one cork cell and one silica cell in single pairs.

Stem Buds

General characteristics: The buds are inserted at or slightly above the edge of the leaf scar. The bud tips generally extend to the growth ring. The buds are medium in size, slightly plump, not protruding. They average 7.2 millimeters wide ×8.2 millimeters high (not including the wing). The central disk of the prophyll is an ovate shape capped by a broad wing.

Wings of the Prophyll: The wings are inserted at or slightly above the middle of the prophyll. The wings are consistently broad on the sides. There is a notch at the tip separating the two lateral halves.

Pubescence. The buds are somewhat fringed with long hairs. Hair groups 1, 4, 10, 11, 15, 19, and 22 are usually prominent.

The Leaf

The Blade: The blades are erect with a drooping tip (see FIG. 9). They are medium to dark green in color. The larger leaves on each stalk are 4.2 to 6.1 centimeters wide averaging 5.1, and are 119.4 to 158.1 centimeters long, averaging 140.5. The ratio of the length of the blade to the width averages 27.7.

The Sheath: The sheaths have an average length of 29.0 centimeters. As the leaves senesce, the top of the sheaths pull away from the stalks, but the base of the sheaths remain attached. The dorsal field of pubescence (group 57) is in a narrow field usually less than 1 centimeter wide, may be sparse, and may not be present on all sheaths. The hairs are sharp and spine like. Hair group 56 is present on covered sheaths, but the associated tissue senesces rapidly upon exposure.

Dewlaps: The dewlaps are generally darker in color than the leaf blade and leaf sheath. They may appear brownish red; the brownish red colors are particularly noticeable in unexposed dewlaps in the whorl. The shape is descending, narrow double crescent.

Auricles: The outer auricle is straight transitional. The area of the inner auricle rapidly senesces after exposure to variability; a distinct lanceolate shape is present in low frequency. When present, the lanceolate auricles vary from 7.5 to 31.0 millimeters in height.

Ligules: The ligule is crescent shaped with a distinct lozenge. It varies from 5.0 to 7.2 millimeters tall at the center.

Inflorescence: Under natural conditions, this new variety has been observed to flower only infrequently in Florida, and only in late season. The inflorescence is average in length and width and moderately thick in appearance compared to a population of Florida clones. The stigma color is maroon and the anther color yellow. (The pollen color was not recorded). The pollen has been viable under controlled conditions where the temperature was maintained above 65° F. during floral development and anther dehiscence.

Important characteristics which, in combination, help to distinguish this variety of sugarcane from all other known varieties are:

(1) Very early maturity.

(2) High sucrose content over a long possible harvest period.

(3) Stalks which bow outwardly from the stool in young cane and usually become recumbent in mature cane.

(4) The internodes are zig zag in alignment.

(5) Stalks with diameters in the middle of the stalks averaging about 27 millimeters ×28 millimeters.

(6) Fiber content of stalks averaging about 10.6%.

(7) Shallow bud furrows of varying lengths present on some of the internodes.

(8) Growth ring about 3 millimeters tall and tumescent.

(9) Root band usually about 6.6 millimeters tall with usually two rows of root primordia, but the upper row may be irregular or lacking.

(10) The stem pattern is type 1 in Artschwager's terminology.

(11) The central disk of prophyll is an ovate shape.

(12) A broad wing is inserted at or slightly above the middle of the prophyll.

(13) The wing of the bud is prominently notched at the apex separating the two lateral buds.

(14) The buds are rather prominently fringed with hairs.

(15) The leaf blades are rather erect with a drooping tip.

(16) The dorsal pubescence of the leaf sheath covers a narrow area, and the hairs are spine like.

(17) The dewlaps are descending narrow double crescent in shape.

(18) The outer auricle is usually straight transitional in shape.

(19) The inner auricle may be lanceolate in shape.

(20) The ligule is crescent-shaped with a distinct lozenge and is usually about 5 to 7 millimeters tall.

In a small plot test over three crops (three crops were harvested from the same plots) on a medium mineral Term Ceia organic soil, the new clone produced 4 percent lower tons per acre of cane, 7 percent higher early tons per acre of sugar (November), and 2 percent higher late tons per acre of sugar (January-February) than the standard cultivar CL61-620. In the same test the new done produced 9 percent higher tons per acre of cane, 17 percent higher early tons per acre of sugar, and 22 percent higher late tons per acre of sugar than the standard cultivar CP70-1133. In a test over three years on a low mineral Terra Ceia organic soil the new clone produced 7 percent lower tons per acre of sugar than standard cultivar CL61-620. In the same test the new cultivar produced 11 percent higher tons cone per acre, 22 percent higher early tons sugar per acre, and 24 percent higher late tons sugar per acre than the standard cultivar CP72-1210.

In one crop of large outfield test on various organic soils west of Lake Okeechobee the new clone produced 10 percent greater tons per acre of cane and 33 percent greater tons per acre of sugar than the standard cultivar CP80-1827. In the same tests the new clone produced 14 percent greater tons per acre of cane and 23 percent greater tons per acre of sugar than the standard cultivar CL61-620. These were conducted on more than 1,000 acres per variety. In one crop of large outfield tests on various organic soils east of Lake Okeechobee the new clone produced 9 percent greater tons per acre of cane, and 14 percent greater tons per acre of sugar than the standard cultivar CP8 1827.In the same tests the now variety produced 11 percent greater tons per acre of cane and 12 percent greater tons per acre of sugar than the standard cultivar CL61-62O. These tests involved over 900 acres per variety.

What is claimed is:

1. The new and distinct variety of sugar cane herein shown, described, and identified by the combination of the characteristics set forth above.

* * * * *